(12) United States Patent
Sugiyama et al.

(10) Patent No.: US 10,730,764 B2
(45) Date of Patent: Aug. 4, 2020

(54) ULTRAVIOLET LIGHT IRRADIATION DEVICE

(71) Applicant: ASAHI KASEI KABUSHIKI KAISHA, Tokyo (JP)

(72) Inventors: Sho Sugiyama, Tokyo (JP); Atsushi Kodama, Tokyo (JP); Naoto Yabuki, Tokyo (JP); Hiroyuki Kishi, Tokyo (JP); Naoto Ito, Tokyo (JP); Sumire Jinno, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/382,505

(22) Filed: Apr. 12, 2019

(65) Prior Publication Data
US 2019/0322546 A1    Oct. 24, 2019

(30) Foreign Application Priority Data

Apr. 20, 2018  (JP) .................................. 2018-081805
Apr. 20, 2018  (JP) .................................. 2018-081806
(Continued)

(51) Int. Cl.
*C02F 1/32*  (2006.01)
*A61L 2/10*  (2006.01)

(52) U.S. Cl.
CPC .............. *C02F 1/325* (2013.01); *A61L 2/10* (2013.01); *A61L 2202/11* (2013.01);
(Continued)

(58) Field of Classification Search
USPC ...................................................... 250/436
See application file for complete search history.

(56) References Cited

U.S. PATENT DOCUMENTS 3,837,800 A * 9/1974 Wood .................. A61L 2/10
                                                                    422/24
4,273,660 A * 6/1981 Beitzel .................. A61L 2/10
                                                                    210/192
(Continued)

FOREIGN PATENT DOCUMENTS

JP       H03-61982 U    6/1991
JP       2003-155721 A  5/2003
(Continued)

OTHER PUBLICATIONS

Extended European Search Report dated Feb. 6, 2020 for application No. 19168922.3, 8 pages.

*Primary Examiner* — Phillip A Johnston
(74) *Attorney, Agent, or Firm* — Morgan, Lewis & Bockius LLP

(57) ABSTRACT

A fluid sterilization module includes an inner cylinder forming a processing flow path, a case portion in which the inner cylinder is accommodated, a member provided between an outer circumferential surface of the inner cylinder and an inner circumferential surface the case portion, a first chamber located in a region on a side of one end portion of the inner cylinder with respect to the member, in a gap between the inner cylinder and the case portion, a second chamber located in a region on a side of the other end portion of the inner cylinder with respect to the member, and a light emitting element provided in at least one of the one end portion and the other end portion of the inner cylinder, and configured to emit ultraviolet light to the object passing through the processing flow path.

19 Claims, 10 Drawing Sheets

(30) Foreign Application Priority Data

Apr. 20, 2018 (JP) .................................. 2018-081808
Apr. 20, 2018 (JP) .................................. 2018-081809

(52) U.S. Cl.
CPC ................... *C02F 2201/328* (2013.01); *C02F 2201/3222* (2013.01); *C02F 2201/3228* (2013.01)

(56) References Cited

U.S. PATENT DOCUMENTS

| | | | |
|---|---|---|---|
| 6,500,346 B1 * | 12/2002 | Taghipour | A61L 2/08 210/198.1 |
| 2012/0318749 A1 | 12/2012 | Stokes et al. | |
| 2014/0240695 A1 | 8/2014 | Pagan et al. | |
| 2015/0114912 A1 * | 4/2015 | Taghipour | C02F 1/325 210/748.11 |
| 2015/0144575 A1 * | 5/2015 | Hawkins, II | A61L 2/10 210/748.11 |
| 2015/0314024 A1 | 11/2015 | Khan et al. | |
| 2017/0290943 A1 | 10/2017 | Stokes et al. | |
| 2018/0147314 A1 | 5/2018 | Stokes et al. | |
| 2018/0257953 A1 | 9/2018 | Mochizuki et al. | |

FOREIGN PATENT DOCUMENTS

| | | |
|---|---|---|
| JP | 5432286 B2 | 12/2013 |
| JP | 2016-511138 A | 4/2016 |
| JP | 6080937 B1 | 1/2017 |
| JP | 2018-202205 A | 12/2018 |

* cited by examiner

FIG. 14A
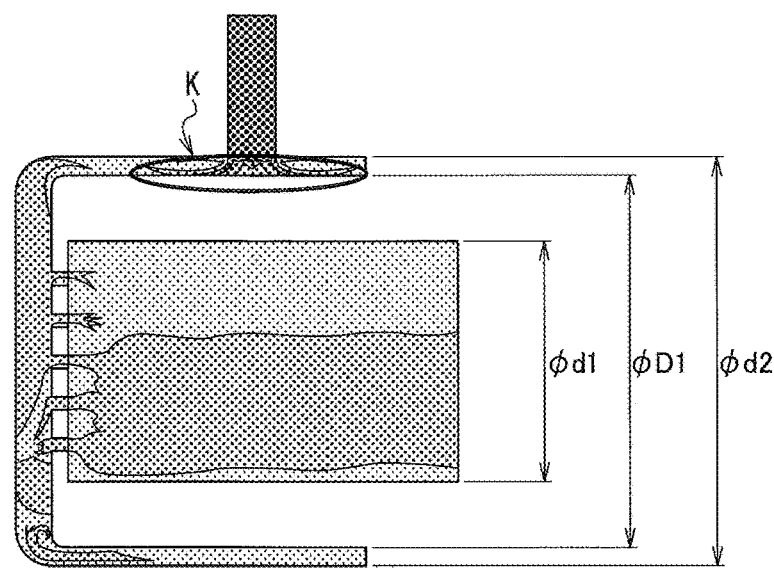
FLUID STERILIZATION MODULE 1-1
FIG. 14B
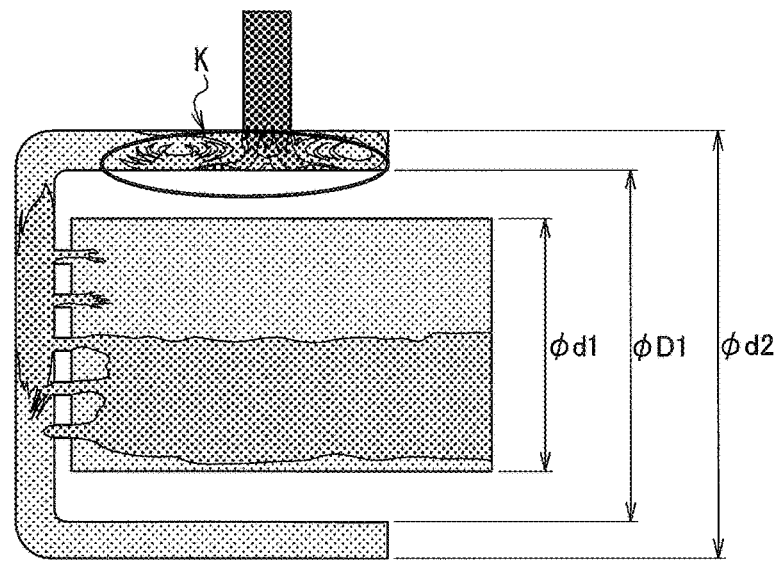
FLUID STERILIZATION MODULE 1-2
FIG. 14C
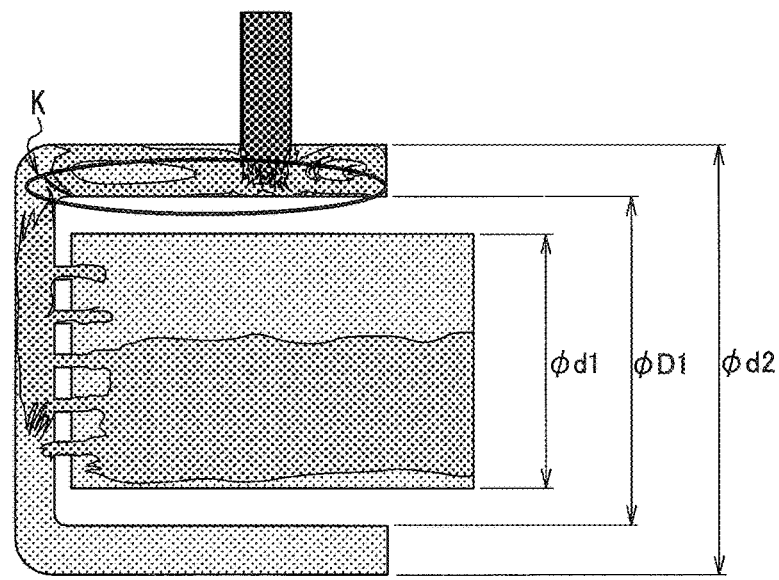
FLUID STERILIZATION MODULE 1-3
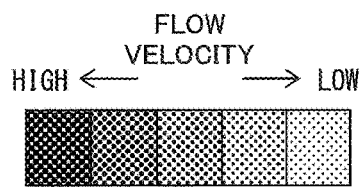

ULTRAVIOLET LIGHT IRRADIATION DEVICE

TECHNICAL FIELD

The present invention relates to ultraviolet light irradiation devices.

BACKGROUND ART

Since ultraviolet light has sterilization capability, various devices for successively sterilizing a fluid such as water, by irradiation of the ultraviolet light, have been proposed.

In existing sterilization devices, a bulb such as a mercury lamp or a xenon lamp is employed as the ultraviolet light source. In addition, a fluid sterilization device has also been proposed that employs a light emitting diode (LED) that emits a light of a wavelength capable of sterilizing, as the ultraviolet light source.

The fluid sterilization devices thus far proposed include, for example, a sterilization device configured to pass an object to be sterilized through a hollow portion of an integrating sphere, and emit the ultraviolet light in the hollow portion thus to sterilize the object (see, for example, Japanese Patent No. 5432286), and a sterilization device including a straight tube constituting a flow path extending in a longitudinal direction, and configured to emit the ultraviolet light in the longitudinal direction to the fluid flowing in the straight tube (see, for example, Japanese Patent No. 6080937).

SUMMARY

However, with the method of utilizing the hollow portion in the integrating sphere as the processing flow path to be irradiated with the ultraviolet light, the hollow portion has to be worked into a complicated shape, because the flow path is surrounded by curved surfaces. The hollow portion in the integrating sphere is normally formed by injection molding. However, most of thermoplastic resins have low reflectance, and also low durability, against ultraviolet light. Accordingly, in the case of adopting, for example, polytetrafluoroethylene (PTFE) as the thermoplastic resin, a machining process has to be performed after forming a simple shape by compression molding or ram extrusion molding, because PTFE is not applicable to melt molding. Therefore, in the case where the processing flow path has a complicated shape, such as the one formed in the integrating sphere, an expensive multi-axis CNC machine has to be employed, and also a long processing time is required. Thus, economic efficiency in manufacturing is degraded.

In the case of the fluid sterilization device that utilizes the straight tube, including a processing flow path having a constant cross-sectional area, the structure is simple and therefore high productivity can be attained, and thus high economic efficiency in manufacturing can be attained. However, PTFE has extremely low adhesiveness owing to the lubricity thereof. Accordingly, even though PTFE is bonded to a member formed of a different material, hydraulic pressure resistance of the joint portion is extremely low. Besides, PTFE has a very narrow elastic deformation region and is therefore prone to incur plastic deformation or creep rupture, which leads to degraded durability of the fluid sterilization device.

The present invention has been accomplished in view of the foregoing problem, and provides an ultraviolet light irradiation device having high robustness, and configured to prevent leakage of a fluid to be sterilized, even though assembly precision is not sufficiently high.

According to an aspect of the present invention, there is provided an ultraviolet light irradiation device including: a cylindrical portion forming a cylindrical processing flow path extending in a longitudinal direction; a case portion in which the cylindrical portion is accommodated; a member of an annular shape, provided in close contact between an outer circumferential surface of the cylindrical portion and an inner circumferential surface the case portion, and including an elastic member at least in a portion in contact with the inner circumferential surface of the case portion; a first chamber located in a region on a side of one end portion of the cylindrical portion with respect to the member, in a cylindrical gap between the cylindrical portion and the case portion; a second chamber located in a region on a side of the other end portion of the cylindrical portion with respect to the member, in the cylindrical gap between the cylindrical portion and the case portion; an inflow portion through which an object flows into the first chamber; an outflow portion through which the object flows out of the second chamber; and a light emitting element provided at least in one of the one end portion and the other end portion of the cylindrical portion, and configured to emit ultraviolet light to the object passing through the processing flow path.

According to another aspect of the present invention, there is provided an ultraviolet light irradiation device including: an ultraviolet light irradiation device comprising: a cylindrical portion forming a cylindrical processing flow path extending in a longitudinal direction, and having an opening in one end portion; a first chamber communicating with the processing flow path via the opening; an inflow portion through which an object flows into the first chamber; a second chamber provided along an outer circumferential surface of the other end portion of the cylindrical portion; a communication port provided in the cylindrical portion, to communicate between the processing flow path and the second chamber; an outflow portion through which the object that has passed through the processing flow path flows out from the other end portion of the cylindrical portion; and a light emitting element provided at least in one of the one end portion and the other end portion of the cylindrical portion, and configured to emit ultraviolet light to the object passing through the processing flow path, wherein the object in the processing flow path flows into the second chamber, only through the communication port.

The mentioned configuration provides an ultraviolet light irradiation device having high robustness, and configured to prevent leakage of a fluid to be sterilized, even though assembly precision is not sufficiently high.

BRIEF DESCRIPTION OF DRAWINGS

FIGS. 14A to 14C are schematic drawings illustrating examples of a simulation result of flow velocity distribution, in the fluid sterilization module.

DESCRIPTION OF EMBODIMENTS

Figure 1:
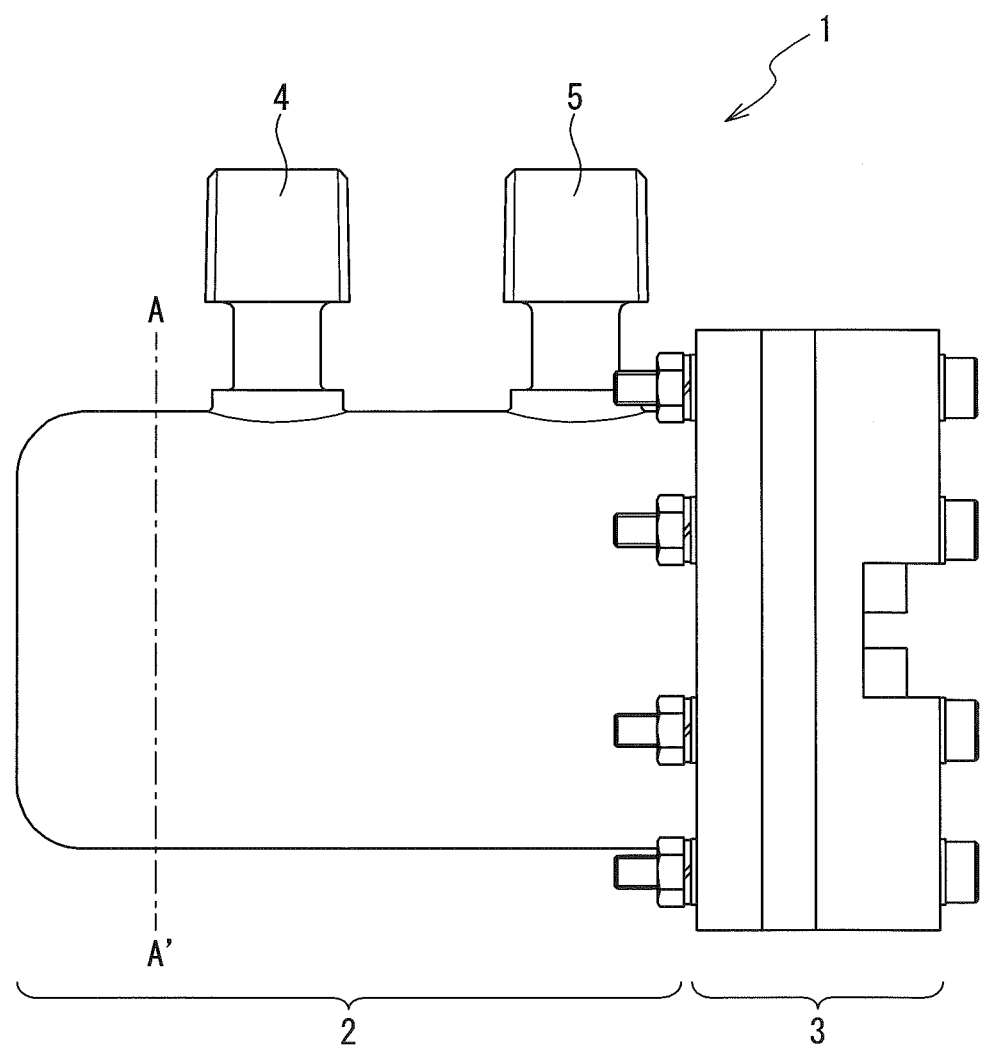
FIG. 1 is a side view illustrating an appearance of a fluid sterilization module, incorporated with an ultraviolet light irradiation device according to the present invention.

Hereafter, an embodiment of the present invention will be described, with reference to the drawings. In the drawings, the same or similar elements are given the same or similar numeral. The drawings are schematically illustrated, and relation between a thickness and a plan-view size, and a thickness ratio among layers, are different from actual ones. In addition, the embodiment described hereunder merely exemplifies devices and methods to realize the technical idea of the present invention, and is in no way intended to limit the material, shape, structure, and location of components to the following embodiment. The technical idea of the present invention may be modified in various manners, within the technical scope defined in the appended claims.

FIG. 1 is a front view illustrating one example of a fluid sterilization module to which an ultraviolet light irradiation device according to the present invention is applied. Additionally, FIG. 2A is a longitudinal cross-sectional diagram of FIG. 1, and FIG. 2B is an end face diagram taken along line A-A' of FIG. 1.

A fluid sterilization module 1 includes a sterilization processing unit 2, a light emitting unit 3, an inflow portion 4, and an outflow portion 5, as illustrated in FIG. 1.

Figure 2A:
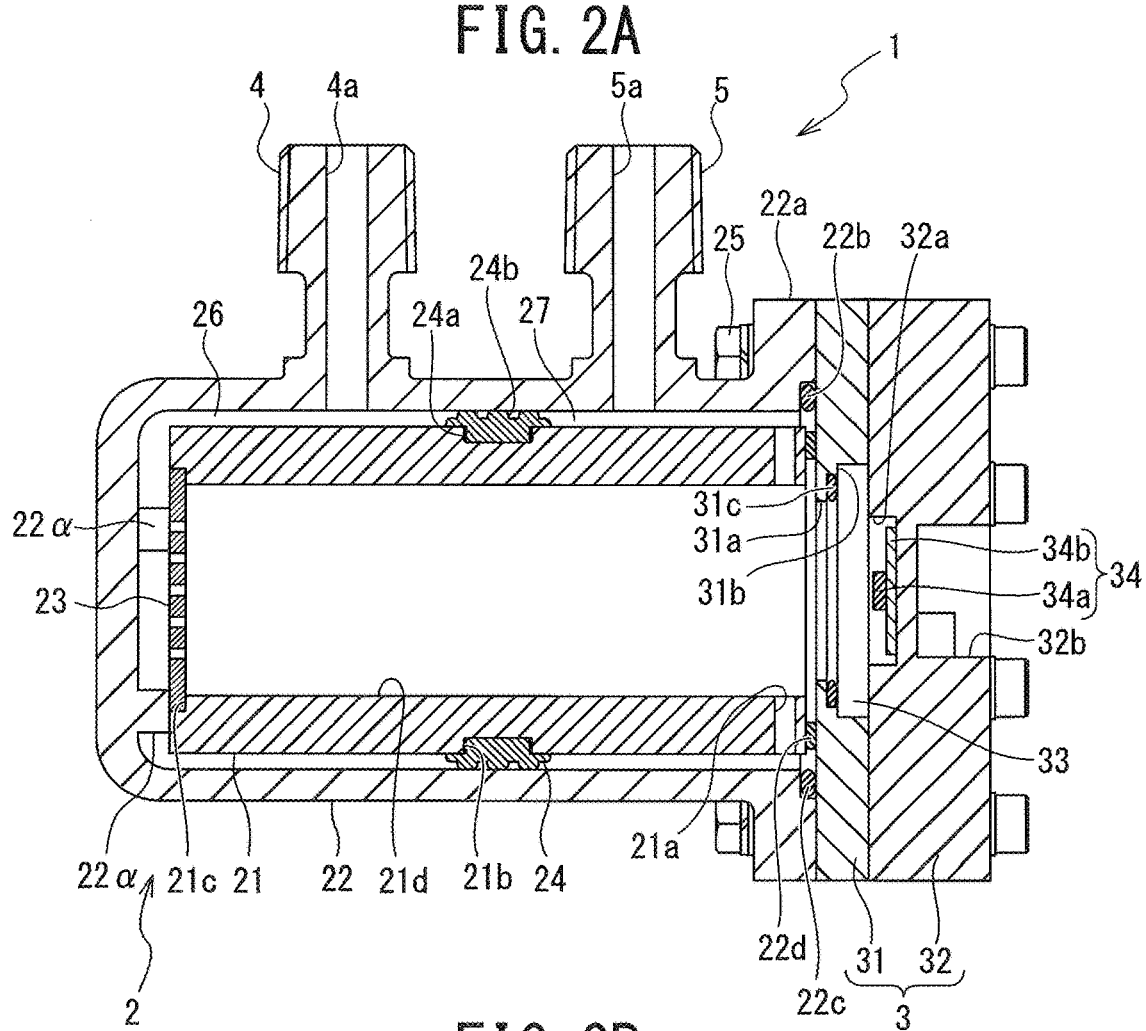
FIG. 2A is a vertical cross-sectional view of FIG. 1.
Figure 2B:
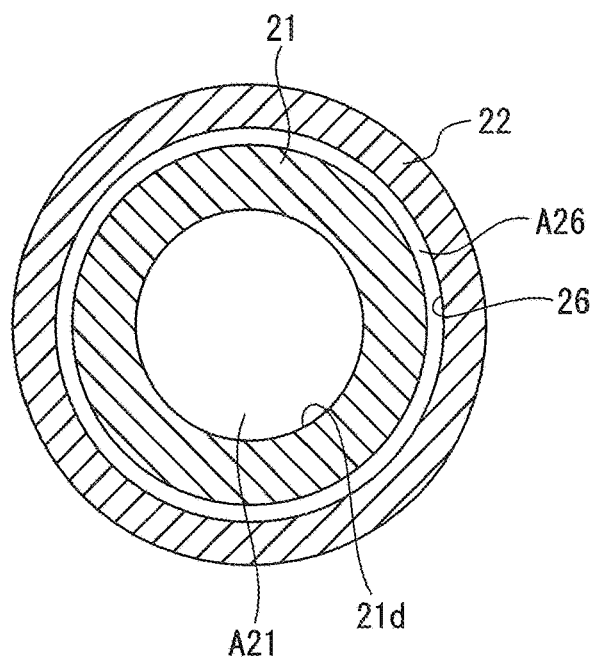
FIG. 2B is a cross-sectional view taken along a line A-A' in FIG. 1.

As illustrated in FIG. 2A, the sterilization processing unit 2 includes an inner cylinder (a cylindrical portion) 21, a case portion 22 housing the inner cylinder 21, a disc-shaped plate 23 fixed to the opening on one end side of the inner cylinder 21 and configured to straighten the flow of a fluid to be flown into the inner cylinder 21, and a member (a member of annular shape) 24 arranged between the inner cylinder 21 and the case portion 22 to partition a gap between the inner cylinder 21 and the case portion 22.

It is preferable that the inner cylinder 21 is formed in a cylindrical shape with open ends, and has a wall thickness equal to or larger than 1 [mm] and equal to or smaller than 20 [mm]. It is also preferable that the inner cylinder 21 is formed of an ultraviolet light reflecting material, having a diffuse transmittance equal to or higher than 1[%]/1 [mm] and equal to or lower than 20[%]/1 [mm], and a total reflectance in an ultraviolet light region equal to or higher than 80[%]/1 [mm] and equal to or lower than 99[%]/1 [mm]. Preferably, further, a sum of the diffuse transmittance and total reflectance in the ultraviolet light region may be equal to or larger than 90[%]/1 [mm]. Examples of the ultraviolet light reflecting materials applicable to the inner cylinder 21 include those including at least one of polytetrafluoroethylene (PTFE), silicone resin, quartz glass containing air bubbles equal to or larger than 0.05 [μm] and equal to or smaller than 10 [μm], partially crystallized quartz glass containing crystallized particles equal to or larger than 0.05 [μm] and equal to or smaller than 10 [μm], an alumina sintered compact including crystallized particles equal to or larger than 0.05 [μm] and equal to or smaller than 10 [μm], and a mullite sintered compact including crystallized particles equal to or larger than 0.05 [μm] and equal to or smaller than 10 [μm].

In the case of employing a diffuse-reflective material to form the inner cylinder 21, the light emitting unit 3, provided at one end portion of the inner cylinder 21, is configured such that at least a part of the irradiation light reaches the other end portion of the inner cylinder 21, on the assumption that the reflective material itself does not absorb the ultraviolet light. When the transmittance under such setting is higher than 20[%]/1 [mm], a very thick material has to be employed to form the inner cylinder 21 with a sufficient wall thickness, to increase effective reflection of the ultraviolet light. In this case, the reflection has to be controlled from a deeper layer, and therefore the optical design becomes difficult, in addition to such disadvantages that the overall size of the fluid sterilization module 1 is increased, and that it becomes difficult to appropriately design the flow path. Although it is basically desirable that a scatterer has a high optical density and low transmittance, a difference in density inside the material, for example between a crystallized portion and non-crystallized portion, constitutes the scatterer in the case of a non-porous material, and therefore it is difficult to attain a structure having a transmittance lower than 1[%]/1 [mm]. In the case of a porous material, although it is possible to attain a structure having a transmittance lower than 1[%]/1 [mm], a processing flow path 21*d*, to be subsequently described, contacts an object to be sterilized (hereinafter simply object, where appropriate), and the minute pores constitute hot beds for germs. Therefore, a porous material is inappropriate to form the inner cylinder 21.

When the total reflectance in the ultraviolet light region is equal to or lower than 80[%]/[mm], a sufficient multiple reflection effect of ultraviolet light is unable to be attained. Although a higher total reflectance is more desirable, a difference in density inside the material, for example between a crystallized portion and non-crystallized portion, constitutes the scatterer in the case of a non-porous material, and therefore it is difficult to attain a structure having the total reflectance higher than 99[%]/1 [mm]. In the case of a porous material, although it is possible to attain a structure having a total reflectance higher than 99[%]/1 [mm], the processing flow path 21*d* contacts the object, and the minute pores constitute hot beds for germs. Therefore, a porous material is inappropriate to form the inner cylinder 21.

Further, when a sum of a diffuse transmittance and a total reflectance in the ultraviolet light region of a material is equal to or smaller than 90[%]/1 [mm], in other words when equal to or larger than 10[%] of energy is absorbed inside, a sufficient multiple reflection effect of ultraviolet light is unable to be attained, and therefore such a material is inappropriate to form the processing flow 21*d*.

Here, the diffuse transmittance is measured with a plate-shaped sample made by slicing an ultraviolet light reflecting material. More specifically, the measurement of the diffuse transmittance of an ultraviolet light reflecting material, for example PTFE, may be performed as described hereunder.

Since PTFE is a diffusive material, it is difficult to properly measure the transmittance, by an ordinary method using linear light. Accordingly, the diffuse transmittance is measured using an integrating sphere. To measure the diffuse transmittance using the integrating sphere, for example a spectrophotometer, popularly used to measure the diffuse transmittance of a suspensible substance, may be utilized as illustrated in FIG. 3.

Figure 3:
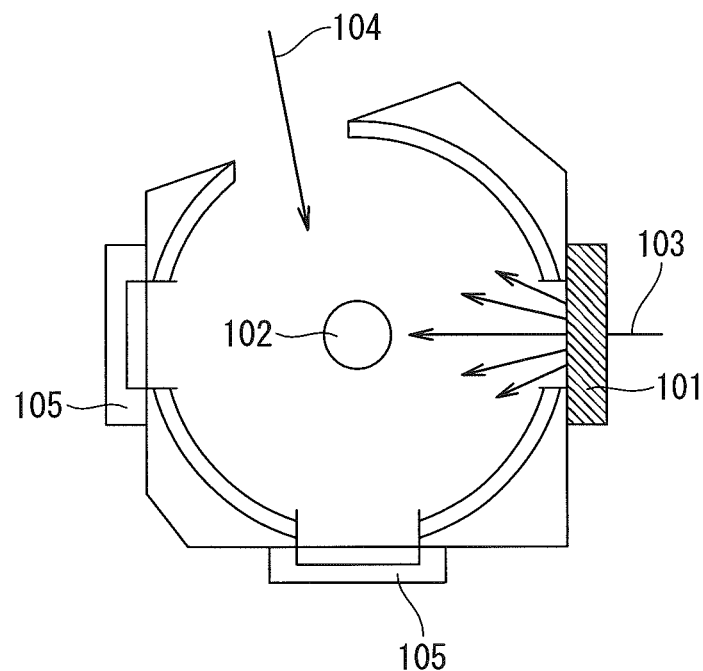
FIG. 3 is a schematic drawing illustrating one example of a device for measuring diffuse transmittance.

In FIG. 3, a reference numeral 101 denotes the plate-shaped sample, 102 denotes a detector, 103 denotes measurement light, 104 denotes contrast light, and 105 denotes a white reflection standard.

Referring again to FIGS. 2A and 2B, it is preferable that the inner cylinder 21 is formed of a material, the outer circumferential surface of which is lower in static friction coefficient than the inner circumferential surface of the case portion 22. To be more detailed, in a first chamber 26, to be subsequently described, defined in a gap between the inner cylinder 21 and the case portion 22, it is preferable that the static friction coefficient of the outer circumferential surface of the inner cylinder 21, constituting the wall face on the inner circumferential side of the first chamber 26, is lower than the static friction coefficient of the inner circumferential surface of the case portion 22, constituting the wall face on the outer circumferential side of the first chamber 26. Under a condition that allows generation of a biofilm, the biofilm is generated earlier on the wall face on the outer circumferential side of the first chamber 26, then on the wall face on the inner circumferential side of the first chamber 26. The biofilm stuck to the wall face on the outer circumferential side of the first chamber 26, in other words on the inner circumferential surface of the case portion 22, forms a shadow when illuminated by a flashlight or the like from outside, and therefore the existence of the biofilm can be confirmed. Thus, the generation of the biofilm in the first chamber 26 can be easily detected. Moreover, the generation of the biofilm can be detected before the biofilm spreads all over the first chamber 26, when the biofilm first appears on the wall face on the outer circumferential side of the first chamber 26, in other words on the inner circumferential surface of the case portion 22. Therefore, the risk originating from the biofilm can be suppressed.

To further reduce the risk originating from the biofilm, it is preferable that the static friction coefficient of the outer circumferential surface of the inner cylinder 21 is equal to or lower than ½ of the static friction coefficient of the inner circumferential surface of the case portion 22. Further, it is more preferable that the static friction coefficient of the outer circumferential surface of the inner cylinder 21 is equal to or lower than 1/10 of the static friction coefficient of the inner circumferential surface of the case portion 22.

Table 1 and Table 2 indicate the friction coefficient of various resins. Table 1 indicates the friction coefficient of resins that are typically employed. Table 2 indicates the static friction coefficient and dynamic friction coefficient of various types of fluororesin.

TABLE 1

| Type of Material | Polymer/Polymer | Polymer/Steel | Steel/Polymer |
|---|---|---|---|
| PTFE | 0.04 | 0.04 | 0.10 |
| Polyethylene | 0.10 | 0.15 | 0.2 |
| Polystyrene | 0.5 | 0.3 | 0.35 |
| Polymethylmethacrylate | 0.8 | 0.5 | 0.45 |

TABLE 2

| Type of Material | Friction Coefficient | |
|---|---|---|
| Fluororesin | Static | Dynamic |
| PTFE | 0.02~0.03 | 0.1~0.2 |
| PFA | 0.05~0.06 | 0.2 |
| FEP | 0.05~0.06 | 0.3~0.4 |
| PCTFE | 0.23~0.36 | 0.15~0.34 |
| ETFE | 0.40 | 0.4 |
| PVDF | 0.3 | 0.14~0.17 |
| PVF | 0.3 | 0.4 |

Referring again to FIG. 2A, the inner cylinder 21 includes six communication ports 21a, each penetrating through the inner cylinder 21 in a radial direction, at a position close to an end portion on the side of the light emitting unit 3, for example at intervals of 60 degrees along the circumferential direction. Here, the location and the number of communication ports 21a are not limited to the above.

It is preferable to form the communication port 21a so as to have a circular cross-section, from the viewpoint of simplicity in machining. Without limitation to the shape having a circular cross-section, the communication port 21a may be formed in a desired shape. It is preferable that the diameter of the communication port 21a is equal to or larger than 1/100 and equal to or smaller than ¼ of the diameter of the processing flow path 21d, and more preferably equal to or larger than 1/20 and equal to or smaller than ⅕.

It is preferable that the communication port 21a is slightly shifted from the end portion on the side of the light emitting unit 3 toward the side of the opposite end portion of the processing flow path 21d with respect to the light emitting unit 3, such that a distance between the center of the opening of the communication port 21a and the end portion of the processing flow path 21d on the side of the light emitting unit 3 is equal to or larger than 1/20 and equal to or smaller than the diameter of the processing flow path 21d. More preferably, the communication port 21a may be slightly shifted from the end portion on the side of the light emitting unit 3 toward the side of the opposite end portion of the processing flow path 21d, such that the mentioned distance is equal to or larger than 1/10 and equal to or smaller than ¼ of the diameter of the processing flow path 21d.

The inner cylinder 21 includes a groove 21b in which the member 24 is fitted, the groove 21b being formed on the outer circumferential surface of the inner cylinder 21, at a central position in the longitudinal direction of the inner cylinder 21. The groove 21b has, for example, a rectangular cross-section.

The inner cylinder 21 also includes a stepped portion 21c to be engaged with the plate 23, formed on the inner circumferential surface of the end portion on the opposite side of the light emitting unit 3. The hollow portion of the inner cylinder 21 constitutes the processing flow path 21d.

Here, from the viewpoint of suppressing the flow velocity of the object in the processing flow path 21d from becoming uneven, it is preferable that a variation range of the main cross-sectional area of the processing flow path 21d, from the most upstream portion, in other words the end portion of the inner circumferential surface of the inner cylinder 21 on the side of the plate 23, to the end portion of the inner circumferential surface of the inner cylinder 21 on the side of the light emitting unit 3, is equal to or smaller than 5%. In addition, it is not mandatory that the processing flow path 21d has a circular cylindrical shape.

The case portion 22 is for example formed of polyolefin, more specifically polypropylene or polyethylene, in a shape having a circular cross-section with a closed end and an open end. The case portion 22 includes a flange portion 22a along the outer circumferential surface of the open end. The case portion 22 also includes a stepped portion 22b along the inner circumferential surface of the open end.

The case portion 22 includes protruding portions 22α formed so as to protrude inwardly of the case portion 22, from the closed end opposite to the open end. The protruding portions 22α are provided at three positions, for example at intervals of 120 degrees along the circumferential direction. The location and the number of protruding portions 22α are not limited to the above, but is suffices that the protruding portions 22α can fix the plate 23, as will be subsequently described.

On the outer circumferential surface of the case portion 22, an inflow portion 4 having therein a cylindrical hollow portion is formed integrally with the case portion 22, at a position close to the closed end. On the outer circumferential surface of the case portion 22, an outflow portion 5 having therein a cylindrical hollow portion is formed integrally with the case portion 22, at a position close to the open end. The opening of the hollow portion of the inflow portion 4 serves as an inflow port 4a, and the opening of the hollow portion of the outflow portion 5 serves as an outflow port 5a.

It is preferable that the inflow portion 4 and the outflow portion 5 are formed such that the direction in which the object flows in the respective hollow portions becomes orthogonal to the longitudinal direction of the case portion 22.

The inflow portion 4 is formed at a position where a distance from the end portion of the outer circumferential surface of the inner cylinder 21 on the side of the stepped portion 21c, toward the end portion of the inner cylinder 21 on the side of the communication port 21a, is equal to or longer than an inflow port-equivalent radius of the inflow port 4a, and equal to or shorter than ⅔ of the processing flow path length in the processing flow path 21d.

The outflow portion 5 is formed at a position where a distance from the communication port 21a toward the end portion of the inner cylinder 21 on the side of the stepped portion 21c is equal to or longer than an outflow port-equivalent radius of the outflow port 5a, and equal to or shorter than ⅔ of the processing flow path length.

Forming the inflow portion 4 and the outflow portion 5 in the respectively mentioned ranges prevents appearance of a portion in the processing flow path 21d where the flow velocity is extremely high.

Further, it is more preferable that the inflow portion 4 is located at a position where a distance from the end portion of the outer circumferential surface of the inner cylinder 21 on the side of the stepped portion 21c, toward the end portion of the inner cylinder 21 on the side of the communication port 21a, is equal to or longer than ½ of an equivalent inner diameter of the processing flow path 21d (hereinafter processing flow path-equivalent inner diameter, where appropriate), and equal to or shorter than ⅔ of the processing flow path length, and even more preferably, equal to or longer than ¾ of the processing flow path-equivalent inner diameter, and equal to or shorter than ⅔ of the processing flow path length.

Likewise, it is more preferable that the outflow portion 5 is located at a position where a distance from the communication port 21a toward the end portion of the inner cylinder 21 on the side of the stepped portion 21c is equal to or longer than ½ of the processing flow path-equivalent inner diameter and equal to or shorter than ⅔ of the processing flow path length, and even more preferably, equal to or longer than ¾ of the processing flow path-equivalent inner diameter, and equal to or shorter than ⅔ of the processing flow path length.

In the case where the inflow portion 4 and the outflow portion 5 are located beyond ⅔ of the processing flow path length, the degree of freedom in designing the locations of the inflow portion 4 and the outflow portion 5 is reduced, which is a reason why the range equal to or smaller than ⅔ of the processing flow path length is preferable.

Figure 4:
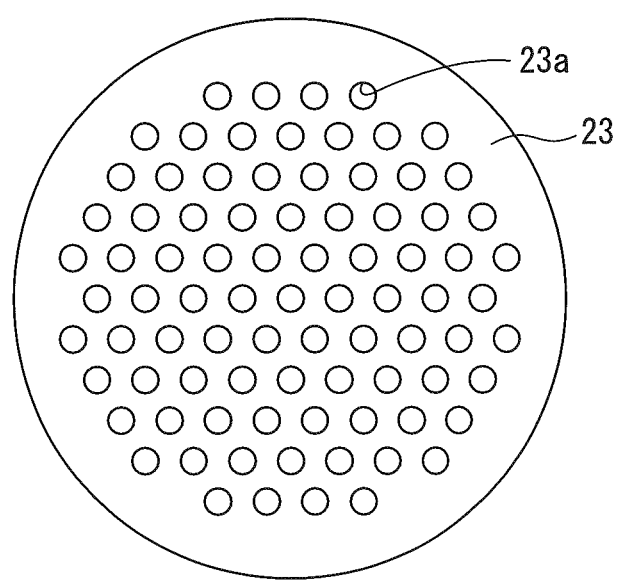
FIG. 4 is a plan view illustrating one example of a plate for flow straightening.

The plate 23 is formed of an ultraviolet light reflecting material, such as PTFE. As the plan view of FIG. 4, the plate 23 includes a plurality of opening holes 23a communicating between the front and rear sides, and the aperture ratio is set to equal to or larger than 0.05 and equal to or smaller than 0.8. In addition, the equivalent diameter of each of the opening holes 23a is set to equal to or larger than 0.5 [mm], and equal to or smaller than ⅓ of the processing flow path-equivalent inner diameter of the processing flow path 21d.

Setting the aperture ratio to equal to or larger than 0.05 and equal to or smaller than 0.8 contributes to improving the flow straightening effect, compared with the case where the first chamber 26, and a second chamber 27 to be subsequently described are not provided. In other words, the flow velocity of the object in the processing flow path 21d can be prevented from becoming uneven. It is preferable that the aperture ratio is equal to or larger than 0.05 and equal to or smaller than 0.6, and more preferably equal to or larger than 0.05 and equal to or smaller than 0.35. In the case where the aperture ratio is below 0.05, the maximum processing capacity with respect to the size of the processing flow path 21d is reduced, which is a reason why it is preferable that the aperture ratio is equal to or larger than 0.05.

Here, although the plate 23 is provided for the purpose of controlling the flow of the object introduced into the processing flow path 21d from the first chamber 26, a flow straightening mechanism capable of straightening the flow may be employed, without limitation to the plate 23 for flow straightening. Alternatively, the plate 23 for flow straightening, or the flow straightening mechanism may be omitted, provided that a required sterilization effect can be attained.

Referring again to FIGS. 2A and 2B, the member 24 is formed of a fluororubber such as Viton (registered trademark). The member 24 is formed in an annular shape, and includes a protruding portion 24a formed on the inner circumferential surface, to be fitted in the groove 21b formed on the inner cylinder 21. On the outer circumferential surface of the member 24, a plurality of (for example, three) annular protruding portions 24b having a semicircular cross-section are formed, so as to be aligned in the width direction.

The member 24 has such a wall thickness in the radial direction that allows the member 24 to closely contact the inner cylinder 21 and the case portion 22, and to define a gap of a predetermined width therebetween.

Then, a region on the side of the closed end of the case portion 22, out of the regions divided by the member 24 in the gap between the inner cylinder 21 and the case portion 22, constitutes the first chamber 26 that serves as an inflow-side flow straightening chamber, defined between the inflow portion 4 and the processing flow path 21d so as to communicate with the opening of the inner cylinder 21 on the side of the stepped portion 21c. Likewise, a region on the side of the open end of the case portion 22, out of the regions divided by the member 24, constitutes the second chamber 27 that serves as an outflow-side flow straightening chamber, defined between the outflow portion 5 and the processing flow path 21d, so as to communicate with the processing flow path 21d via the communication ports 21a.

The first chamber 26 is configured to have an inner volume equal to or larger than ⅔ (approximately 67[%]) of a cube of the processing flow path-equivalent inner diameter of the processing flow path 21d, and equal to or smaller than 3 times of the inner volume of the processing flow path in the processing flow path 21d. Setting the inner volume of the first chamber 26 to the mentioned range contributes to improving the flow straightening effect, compared with the case where the first chamber 26 and the second chamber 27 are not provided. Here, it is preferable to make the inner volume of the first chamber 26 equal to or larger than 75[%] of the cube of the processing flow path-equivalent inner diameter, and equal to or smaller than 2 times of the inner volume of the processing flow path, and more preferably, processing flow path inner volume equal to or smaller than 85[%] of the cube of the processing flow path-equivalent inner diameter, and equal to or smaller than the inner volume of the processing flow path. In the case where the inner volume of the first chamber 26 is larger than 3 times of the inner volume of the processing flow path, the overall size of the fluid sterilization module 1 becomes excessively large with respect to the processable flow rate, which is a reason why it is preferable that the inner volume of the first chamber 26 is equal to or smaller than 3 times of the inner volume of the processing flow path.

Further, it is preferable that the cross-sectional area A26 of the first chamber 26, illustrated in FIG. 2B, is equal to or larger than 1/10, and equal to or smaller than 1 of the cross-sectional area A21 of the processing flow path 21d, and more preferably equal to or larger than 1/10, and equal to or smaller than ½. When the cross-sectional area A26 of the first chamber 26 is smaller than 1/10 of the cross-sectional area A21 of the processing flow path 21d, it is difficult to allow the fluid sterilization module 1 to perform the expected function, and when the cross-sectional area A26 is larger than the cross-sectional area A21, it is difficult to effectively prevent the generation of the biofilm.

To be more detailed, it will be assumed that, when the processing capacity for sterilization by the fluid sterilization module 1 is 2 [L/min], the cross-sectional area necessary for sterilization, in other words the cross-sectional area A21 of the processing flow path 21d is larger than 3.14 [cm$^2$], and the cross-sectional area A26 of the first chamber 26 necessary for preventing the generation of the biofilm is smaller than 1.53 [cm$^2$]. These relative values are considered to be proportional to the flow rate, and therefore when the processing capacity is X [L/min], the cross-sectional area A21 of the processing flow path 21d necessary for sterilization can be expressed as A21>1.57×X [cm$^2$], and the cross-sectional area A26 of the first chamber 26 necessary for preventing the generation of the biofilm can be expressed as A26<0.76×X [cm$^2$]. Accordingly, it is preferable that the value obtained by dividing "cross-sectional area A21 necessary for sterilization" by "cross-sectional area A26 necessary for preventing generation of biofilm" is larger than 2.06 ((A21/A26)>2.06). Here, the length of the processing flow path 21d is determined on the basis of the transmittance of the object, and does not depend on the target processing capacity.

Figure 5:
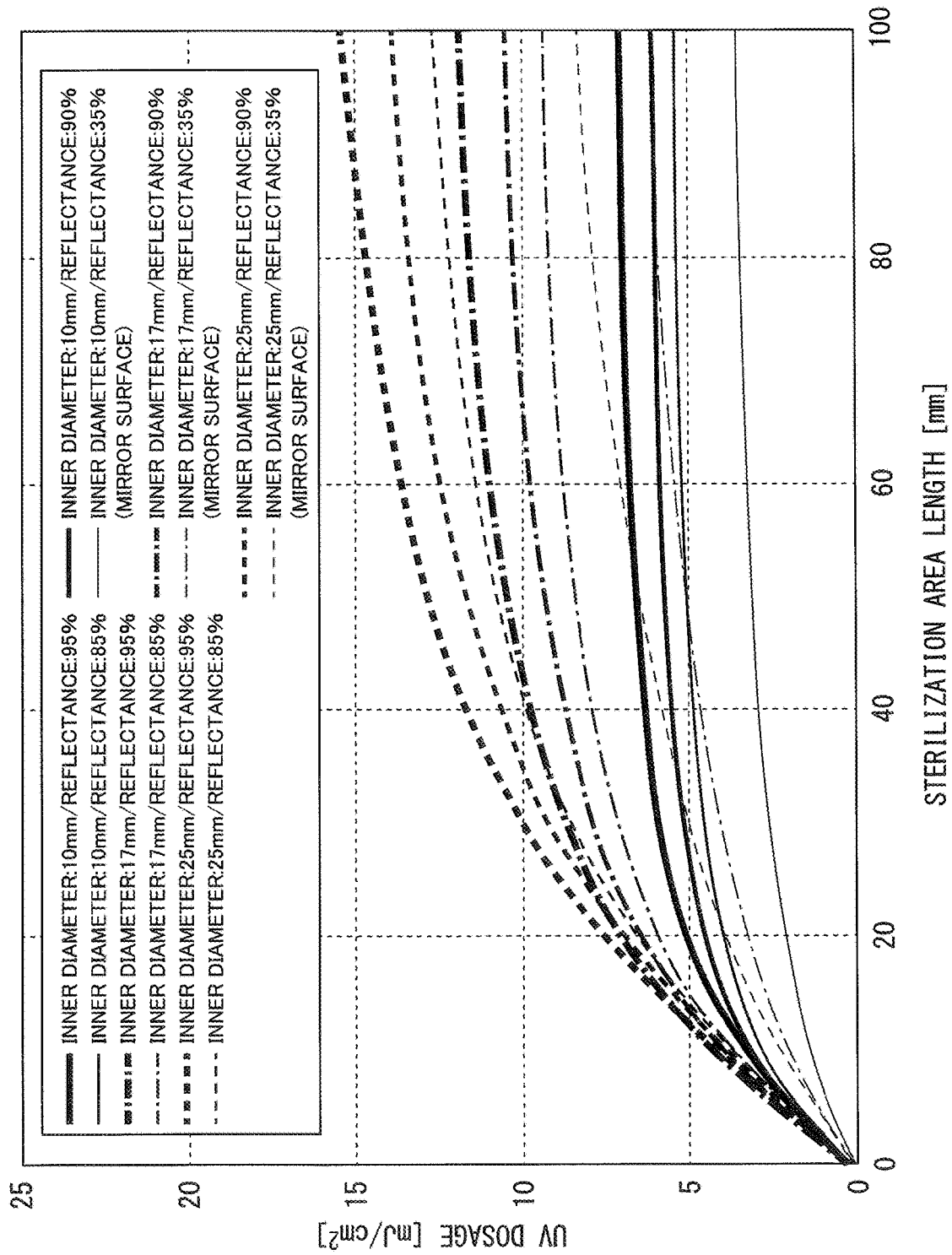
FIG. 5 illustrates one example of a characteristic graph indicating relations between a length of a sterilization area and dosage of ultraviolet light necessary for sterilization.

FIG. 5 is a characteristic graph indicating the relation between the length of the sterilization area, in other words the length of the processing flow path 21d, and dosage (cumulative irradiation dose) of ultraviolet light absorbed by the fluid and utilized for sterilization. In FIG. 5, the horizontal axis represents the length (mm) of the sterilization area, and the vertical axis represents the dosage (cumulative irradiation dose) (mJ/cm$^2$) of the ultraviolet light. The characteristic lines respectively correspond to different inner diameters and different reflectance values of the processing flow path 21d. When the inner diameter and the reflectance of the processing flow path 21d are given, the length of the processing flow path 21d and the dosage (cumulative irradiation dose) of ultraviolet light can be determined, on the basis of FIG. 5. Realizing thus both of the flow velocity that prevents the generation of the biofilm, and the dosage that secures a certain sterilization capability, enables a stabilized sterilization capability to be provided for an extended period of time.

The material of the member 24 is not limited to fluororubber, but any desired material may be adopted, provided that the material can divide the gap between the inner cylinder 21 and the case portion 22, to restrict the object from flowing back and forth between the closed end and the open end of the case portion 22, and has durability.

The number of protruding portions 24b formed on the member 24 is not limited to three, but may be any number not less than two. Providing a plurality of protruding portions 24b allows the inner cylinder 21 and the case portion 22 to be stably fixed. The protruding portions 24b may be aligned in the width direction, for example at regular intervals, so as to secure a gap of a constant width between the inner cylinder 21 and the case portion 22, instead of making the gap uneven because of a biased location of the protruding portions 24b.

It is to be noted that the term "equivalent inner diameter" or "equivalent diameter" herein refers to "quadruple of the flow path cross-sectional area/flow path cross-sectional circumferential length".

The term "equivalent radius" refers to "twice the flow path cross-sectional area/flow path cross-sectional circumferential length".

In addition, the flow straightening chamber refers to a space located between the processing flow path and an external device, including the inflow port and the outflow port for supplying and receiving the object between the fluid sterilization module 1 and the external device, and having an equivalent inner diameter equal to or larger than 110%, more preferably equal to or larger than 150% of the processing flow path-equivalent inner diameter.

Referring again to FIG. 2A, the light emitting unit 3 includes a window portion (covering the entire opening) 31 and an element unit 32.

The window portion 31 is formed of stainless steel for example, in an annular shape having the same outer diameter as that of the flange portion 22a of the case portion 22. The window portion 31 includes a first stepped portion 31a, and a second stepped portion 31b larger in diameter than the first stepped portion 31a, formed on the inner circumferential surface. A disk-shaped window 33, formed of an ultraviolet light transmissive material such as quartz glass, is fitted in the second stepped portion 31b, so as to be flush with the surface of the window portion 31 on the side of the element unit 32.

The element unit 32 is formed of stainless steel for example, in an annular shape having the same outer diameter as that of the window portion 31. A recess 32a of a circular shape in a plan view is formed on the surface of the element unit 32 opposing the window portion 31. A light source 34, including a light emitting element 34a constituted of an UVC-LED (deep UV LED) or the like, and a substrate 34b on which the light emitting element 34a is mounted, is fixed to the recess 32a such that the light-emitting surface is opposed to the window 33. The light source 34 is located such that the optical axis of the light emitted from the light source 34 coincides with the central axis of the processing flow path 21d in the longitudinal direction.

The element unit 32 includes a recess 32b formed on the opposite side of the window portion 31, in which a control circuit board, having a non-illustrated control device and other components mounted thereon, is to be fixed.

The sterilization processing unit 2 and the light emitting unit 3 are coupled to each other by through bolts 25, at the flange portion 22a of the case portion 22.

In addition, an O-ring 22c formed of an elastic member such as rubber is provided on the stepped portion 22b, and an annular elastic sheet 22d formed of an elastic member is provided between the end portion of the inner cylinder 21 on the side of the communication port 21a and the window portion 31, to prevent the object from leaking outward through the contact interface between the window portion 31 and the case portion 22. To form the elastic sheet 22d, it is preferable to employ an elastomer such as a silicone resin elastomer or a fluororesin elastomer.

By fastening the through bolts 25 with the elastic sheet 22d interposed between the end portion of the inner cylinder 21 on the side of the communication port 21a and the window portion 31, the plate 23 attached to the stepped portion 21c of the inner cylinder 21 is pressed by the protruding portion 22a, so as to be held between the protruding portion 22a and the stepped portion 21c. Thus, the plate 23 is fixed to the stepped portion 21c.

In addition, an O-ring 31c formed of an elastic member such as rubber is provided between the first stepped portion 31a and the window 33 of the window portion 31, to prevent the object from leaking outward through the contact interface between the window portion 31 and the window 33.

The width of a gap between the end portion of the inner cylinder 21, and a region of the window portion 31 opposed to the end portion of the inner cylinder 21 via the elastic sheet 22d, may be set to equal to or narrower than 25 [μm], from the viewpoint of the accuracy in machining. Further, with the width equal to or narrower than 10 [μm], leakage of the object, typically water, can be substantially restricted, because of the surface tension of the object.

Advantageous Effects (1) In the fluid sterilization module 1 according to the embodiment of the present invention, the gap between the inner cylinder 21 and the case portion 22 is divided by the member 24, into the spaces on the side of the inflow portion 4 and on the side of the outflow portion 5. Accordingly, the object can be prevented from leaking from the flow path, such as the first chamber 26 and the second chamber 27, despite the assembly precision not being sufficiently high. In addition, since mentioned spaces can be obtained simply by interposing the member 24 between the inner cylinder 21 and the case portion 22, a significant increase of the manufacturing process can be avoided. Further, since the member 24 is formed of an elastic member, the fluid sterilization module can also exhibit, for example, excellent robustness during the actual operation.

(2) In the fluid sterilization module 1 according to the embodiment of the present invention, the object that has passed through the processing flow path 21d can flow out to the second chamber 27, only through the communication port 21a located close to the end portion of the inner cylinder 21 on the side of the light emitting unit 3, to flow out through the outflow portion 5. The entirety of the object that has passed through the processing flow path 21d flows out only through the communication port 21a. Accordingly, even when the flow rate fluctuates, the flow velocity distribution in the processing flow path 21d can be suppressed from fluctuating owing to the fluctuation of the flow rate. The mentioned configuration thus prevents imperfect sterilization, originating from the fluctuation of the flow velocity distribution.

(3) The fluid sterilization module 1 according to the embodiment of the present invention includes the first chamber 26 having a certain level of volume, located upstream of the processing flow path 21d. Accordingly, even though the assembly precision is uneven among the products, the impact of the unevenness in assembly precision can be mitigated, by causing the object to flow into the processing flow path 21d through the first chamber 26. As result, unevenness in flow velocity of the object in the processing flow path 21d can be suppressed. Consequently, unevenness in quality of the fluid sterilization module 1, originating from uneven assembly precision among the individual products, can be suppressed.

(4) In the fluid sterilization module 1 according to the embodiment of the present invention, the cross-sectional area A26 of the first chamber 26 is equal to or larger than $\frac{1}{10}$ and equal to or smaller than 1, more preferably equal to or larger than $\frac{1}{10}$ and equal to or smaller than $\frac{1}{2}$, of the cross-sectional area A21 of the processing flow path 21d. Therefore, the sterilization effect can be attained in the processing flow path 21d, and also generation of the biofilm in the first chamber 26 can be prevented.

In addition, the inner cylinder 21 is formed of a material having a lower static friction coefficient on the outer circumferential surface, than the static friction coefficient of the inner circumferential surface of the case portion 22. Therefore, the generation of the biofilm can be easily detected and, moreover, the generation of the biofilm can be detected before the biofilm spreads all over the first chamber 26, when the biofilm first appears on the inner circumferential surface of the case portion 22. The mentioned configuration contributes, therefore, to minimizing the risk originating from the biofilm.

Here, the generation status of the biofilm stuck to the surface of the case portion 22 can be confirmed, for example in the occasion of periodical maintenance of the fluid sterilization module 1, by bringing a light source such as a flashlight close to the outer circumferential surface of the case portion 22, thereby visually checking a stain utilizing reflection from the inner side of the case portion 22.

On the side of the inner cylinder 21, the first chamber 26 serving as the inflow-side flow straightening chamber and the second chamber 27 serving as the outflow-side flow straightening chamber are provided between the inner cylinder 21 and the case portion 22. Accordingly, fluid layers different in refractive index from each other are created. Therefore, the biofilm stuck to the inner cylinder 21 is unable to be visually recognized from outside of the case portion 22. In other words, even though the biofilm is stuck to the inner cylinder 21, it is difficult to visually recognize the presence of the biofilm. For such reason, it is very important, from a practical point of view, to take a measure to retard the generation of the biofilm on the side of the inner cylinder 21, compared with the side of the case portion 22. Thus, it can be assumed that the biofilm has not yet been generated on the side of the inner cylinder 21, at the time point that the biofilm stuck to the case portion 22 is detected. Therefore, when the biofilm stuck to the case portion 22 is detected, the removal of the biofilm, if any, from the inner cylinder 21 may also be performed, at the same timing.

As described above, the fluid sterilization module 1 according to the embodiment of the present invention can suppress the generation of the biofilm in the first chamber 26. Therefore, a decline in sterilization effect originating from the presence of the first chamber 26 can be further minimized.

(5) In the fluid sterilization module 1 according to the embodiment of the present invention, the inner cylinder 21 has a wall thickness equal to or thicker than 1 [mm], and equal to or thinner than 20 [mm], and includes an ultraviolet light reflecting material having a diffuse transmittance equal to or higher than 1[%]/1 [mm], and equal to or lower than 20[%]/1 [mm], and a total reflectance in a ultraviolet light region equal to or higher than 80[%]/1 [mm], and equal to or lower than 99[%]/1 [mm].

Figure 6:
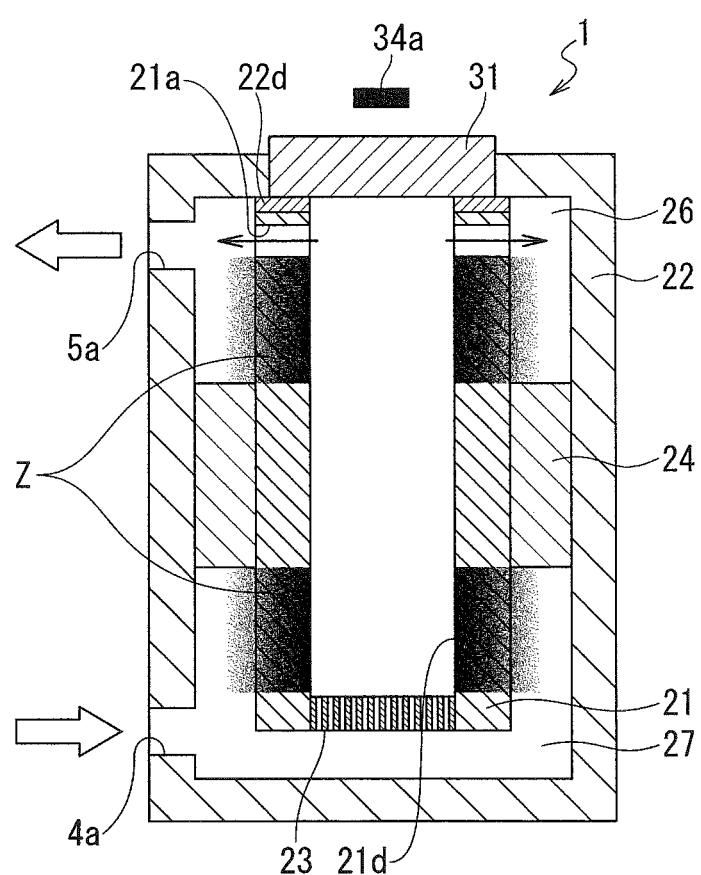
FIG. 6 is a schematic drawing for explaining transmission status of ultraviolet light.

The mentioned configuration enables the ultraviolet light emitted from the light emitting unit 3 to the processing flow path 21$d$ to be locked inside the processing flow path 21$d$ in high density, thereby allowing the ultraviolet light to exhibit high sterilization capability. In addition, since the inner cylinder 21 transmits a part of the ultraviolet light, the ultraviolet light emitted into the processing flow path 21$d$ is transmitted through the inner cylinder 21, and emitted into the first chamber 26 and the second chamber 27, as indicated by a reference code Z in FIG. 6. Thus, the fluid in the first chamber 26 and the second chamber 27 is also irradiated with the ultraviolet light, and therefore proliferation of germs on the object stored in the first chamber 26 and the second chamber 27 can be prevented. Therefore, even when the object resides in the first chamber 26 and the second chamber 27, proliferation of germs in these chambers can be suppressed, and also the object on which the germs have proliferated can be prevented from flowing out, when the flow is started. Consequently, the reliability of the fluid sterilization module 1 can be further upgraded. Here, FIG. 6 is a simplified drawing of the fluid sterilization module 1 of FIG. 2A.

[Variation]

Although the foregoing embodiment refers to the case where the ultraviolet light irradiation device is configured as a fluid sterilization module for sterilization of a fluid, the object to be sterilized may be a fluid such as water, aqueous solution, or colloidal dispersion, gas such as air, or fine powder of ice or a solid matter.

In the foregoing embodiment, the protruding portion 24$a$ is provided on the inner circumferential surface of the member 24, and the plurality of protruding portions 24$b$ are provided on the outer circumferential surface, however a different configuration may be adopted. The member 24 may be formed in any desired shape, provided that the member can be restricted from moving in the longitudinal direction of the inner cylinder 21, by being fitted in the groove 21$b$ formed on the outer circumferential surface of the inner cylinder 21, that the member 24 can restrict the object from moving between the spaces divided by the member 24, through the contact interface between the member 24 and the inner cylinder 21, and the contact interface between the member 24 and the case portion 22, and that the member 24 has sufficient durability.

Figure 7:
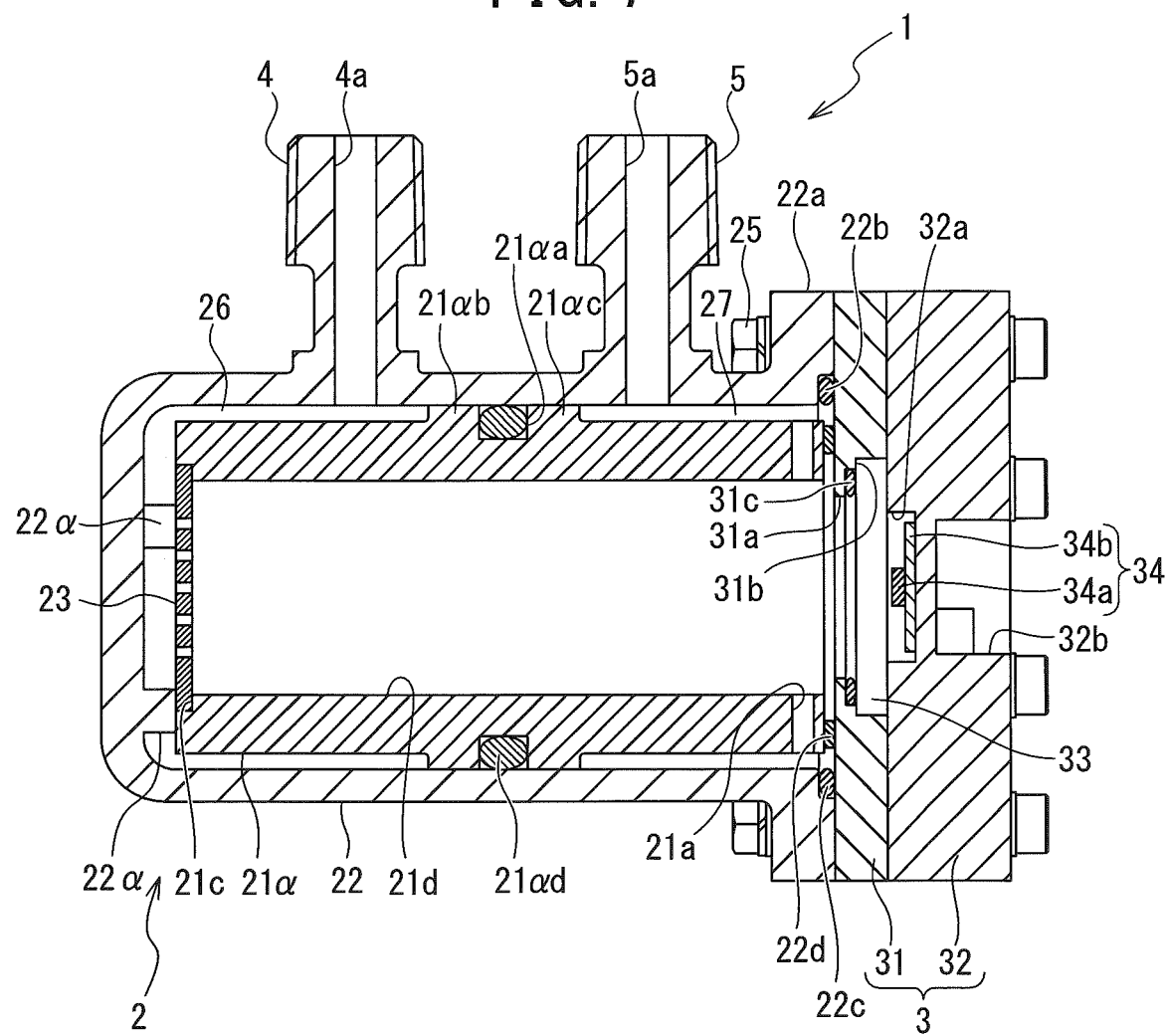
FIG. 7 is a cross-sectional view illustrating a variation of the fluid sterilization module.

For example, an inner cylinder 21α illustrated in FIG. 7 may be employed, in place of the inner cylinder 21 of FIG. 2A. The inner cylinder 21α includes, as illustrated in FIG. 7, an annular groove 21αa formed on the outer circumferential surface, at a central position in the longitudinal direction of the inner cylinder 21α, and annular protruding portions 21αb and 21αc formed on the respective sides of the groove 21αa. The protruding portions 21αb and 21αc are formed in such a height that allows the outer circumferential surface of the protruding portions 21αb and 21αc and the inner circumferential surface of the case portion 22 to abut against each other. In addition, an O-ring 21αd formed of an elastic member such as rubber is fitted in the groove 21αa. When the inner cylinder 21α thus configured is set inside the case portion 22, the outer circumferential surface of the protruding portions 21αb and 21αc, and the O-ring 21αd contact the inner circumferential surface of the case portion 22, and a gap is defined between the case portion 22 and the inner cylinder 21α, on the side of the inflow portion 4 from the protruding portion 21αb, as well as on the side of the outflow portion 5 from the protruding portion 21αc. The gap on the side of the inflow portion 4 from the protruding portion 21αb constitutes the first chamber 26, and the gap on the side of the outflow portion 5 from the protruding portion 21αc constitutes the second chamber 27.

With the inner cylinder 21α configured as above also, the same advantageous effects as described above can be attained.

Further, although the gap between the inner cylinder 21 and the case portion 22 is divided into two sections by the member 24 as illustrated in FIG. 2A, and one of the divided section serves as the first chamber 26, and the other serves as the second chamber 27, a different configuration may be adopted. For example, the first chamber 26 and the second chamber 27 may each be formed as independent components.

In the foregoing embodiment, the light emitting element 34$a$ is provided on the end portion of the processing flow path 21$d$ opposite to the plate 23. However, the light emitting element 34$a$ may be provided on the side of the plate 23 instead, or both on the side of the plate 23 and on the opposite side.

Although the embodiment of the present invention has been described as above, it should be noted that the foregoing embodiment merely exemplifies the devices and the methods to realize the technical idea of the present invention, and is in no way intended to limit the material, shape, structure, and location of the components to the foregoing embodiment. The technical idea of the present invention may be modified in various manners, within the technical scope defined in the appended claims.

EXAMPLES

Hereunder, Examples of the fluid sterilization module 1 incorporated with the ultraviolet light irradiation device according to the present invention will be described.

Example A

Sterilization efficiency was detected, with respect to fluid sterilization modules configured as Examples A1 to A3, each incorporated with the fluid sterilization module 1 according to the present invention, and fluid sterilization modules configured as Comparative Examples A1 and A2.

To measure the sterilization efficiency, a solution of 25[° C.], transmittance 97[%/cm], and *E. Coli* NBRC3972 ($1\times10^6$ [CFU/ml]) was prepared, and the solution was introduced through the inflow portion 4 at a flow velocity of 2.0 [L/min]. Two light emitting elements 34$a$ were employed as the light source 34, and a light source that outputs ultraviolet light of 35 [mW] from a pulse current of 500 [mA] was employed as the light emitting element 34a. The pulse current was selected for emission measurement, to confirm the optical output of the light emitting element without depending on heat, and the sterilization was performed with continuous emission created by continuous current. Residual germs [%] and a logarithm reduction value (LRV) were measured as the sterilization efficiency. LRV can be obtained through the following equation (1).

$$LRV = -\log(\text{number of germs in sterilized solution} / \text{number of germs in original liquid(solution)}) \quad (1)$$

In FIG. 8 to FIG. 12, the fluid sterilization module 1 is illustrated in a simplified manner.

Example A1

Figure 8:
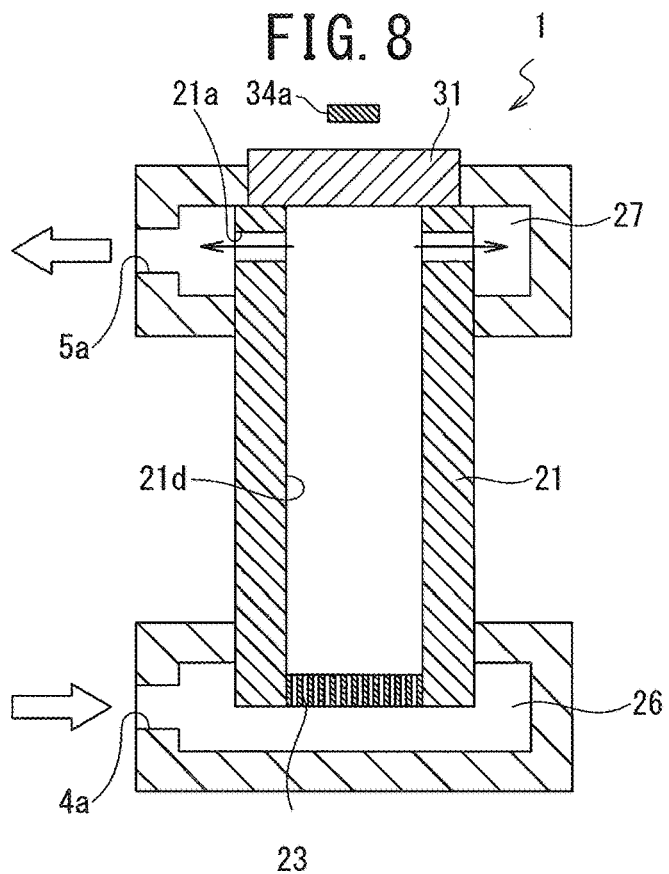
FIG. 8 is a schematic drawing illustrating a general configuration of a fluid sterilization module according to Example A1.

In the fluid sterilization module 1 according to Example A1, the first chamber 26 and the second chamber 27 are respectively provided, as illustrated in FIG. 8, at the end portion of the inner cylinder 21 on the side of the inflow portion 4, and at the end portion on the side of the outflow portion 5. The first chamber 26 and the second chamber 27 are each formed as an independent component, and located only around each of the end portions on the side of the inflow portion 4 and the outflow portion 5 of the inner cylinder 21, so as to surround the opening and the outer circumferential surface. In addition, the plate 23 is provided on the opening of the inner cylinder 21 on the side of the inflow portion 4.

Example A2

Figure 9:
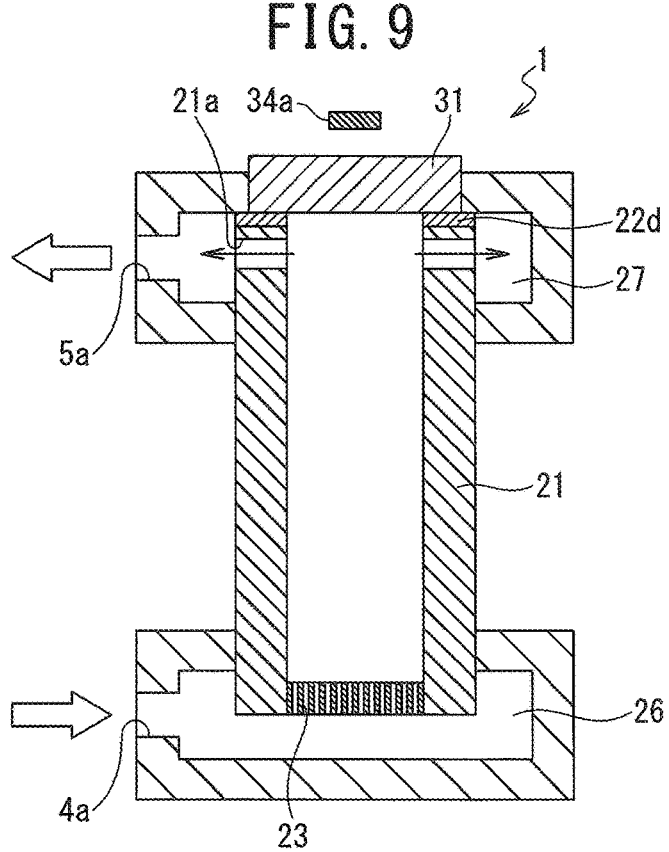
FIG. 9 is a schematic drawing illustrating a general configuration of a fluid sterilization module according to Example A2.

In the fluid sterilization module 1 according to Example A2, the elastic sheet 22d is further provided, as illustrated in FIG. 9, between the window portion 31, including the window 33 formed of quartz glass or the like, and the end face of the inner cylinder 21, in addition to the configuration of the fluid sterilization module 1 according to Example 1.

Example A3

Figure 10:
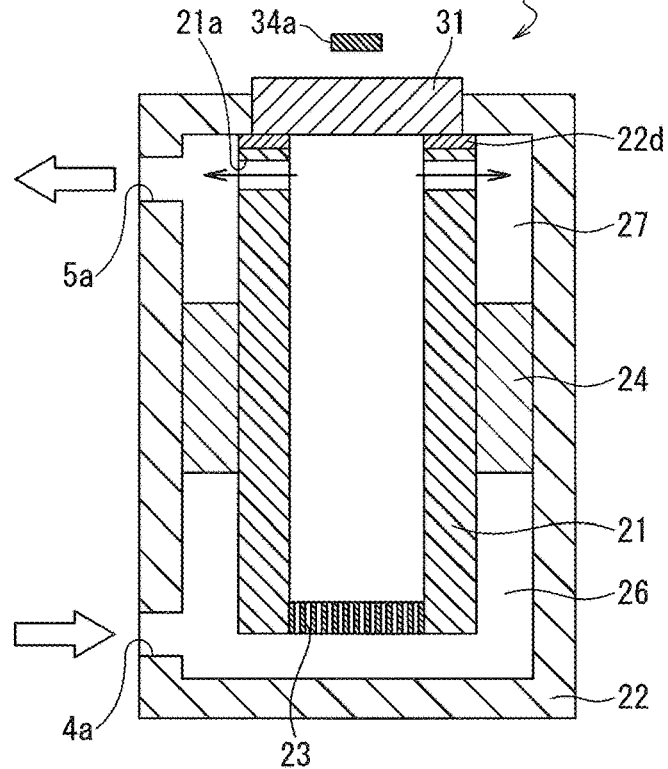
FIG. 10 is a schematic drawing illustrating a general configuration of a fluid sterilization module according to Example A3.

The fluid sterilization module 1 according to Example A3 corresponds, as illustrated in FIG. 10, to the fluid sterilization module 1 of FIGS. 2A and 2B.

Comparative Example A1

Figure 11:
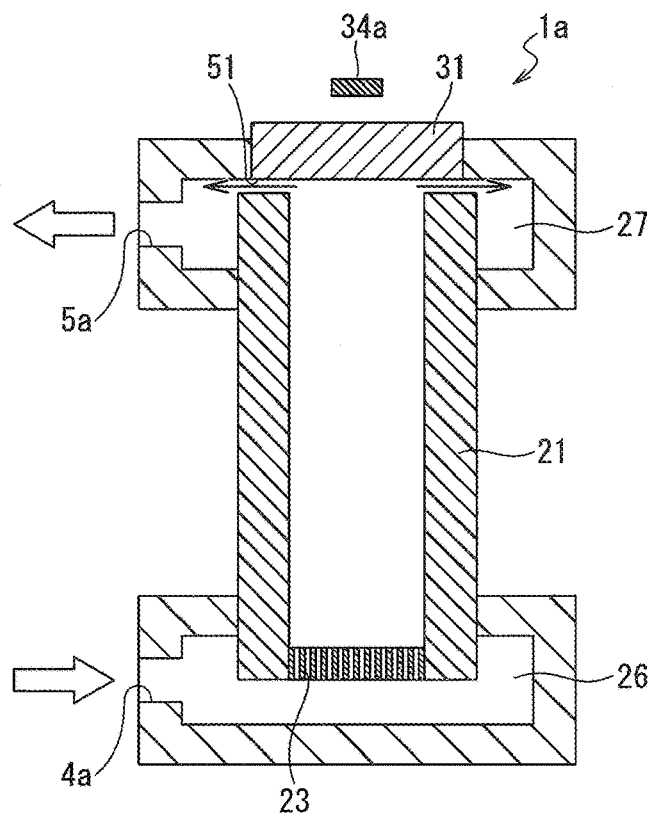
FIG. 11 is a schematic drawing illustrating a general configuration of a fluid sterilization module according to Comparative Example A1.

In the fluid sterilization module 1a according to Comparative Example A1, a gap 51 is provided, as illustrated in FIG. 11, between the inner cylinder 21 and the window portion 31, in place of the communication port 21a, in the fluid sterilization module 1 according to Example 1, to allow the object that has passed through the processing flow path 21d to flow out through the outflow portion 5, through the gap 51.

Comparative Example A2

Figure 12:
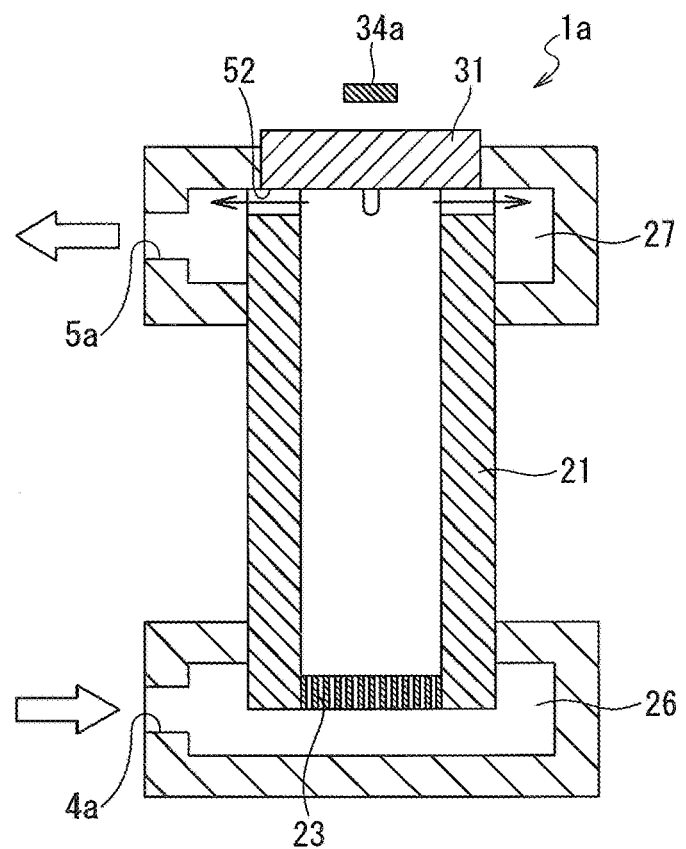
FIG. 12 is a schematic drawing illustrating a general configuration of a fluid sterilization module according to Comparative Example A2.

In the fluid sterilization module 1a according to Comparative Example A2, a groove 52 extending in a radial direction is formed, as illustrated in FIG. 12, on the end portion of the inner cylinder 21 on the side of the window portion 31, instead of the gap 51, in the fluid sterilization module 1a according to Comparative Example A1, to allow the object that has passed through the processing flow path 21d to flow out through the outflow portion 5, through the flow path formed between the window portion 31 and the groove 52 of the inner cylinder 21.

Sterilization Efficiency

Table 3 indicates the measurement results of the sterilization efficiency, with respect to Examples A1 to A3 and Comparative Examples A1 and A2.

As is apparent from Table 3, the residual germs % was significantly reduced in the fluid sterilization module 1 according to Examples A1 to A3, compared with the fluid sterilization module 1a according to Comparative Examples A1 and A2. It is also apparent that the values of LRV are higher in the fluid sterilization module 1 according to Examples A1 to A3, than in the fluid sterilization module 1a according to Comparative Examples A1 and A2.

TABLE 3

|  | Example A1 | Example A2 | Example A3 | Comparative Example A1 | Comparative Example A2 |
|---|---|---|---|---|---|
| Residual Germs % | 0.00038% | 0.00031% | 0.000083% | 3.8% | 0.037% |
| LRV | 5.4 | 5.5 | 6.1 | 1.4 | 3.4 |

Example B

Figure 13:
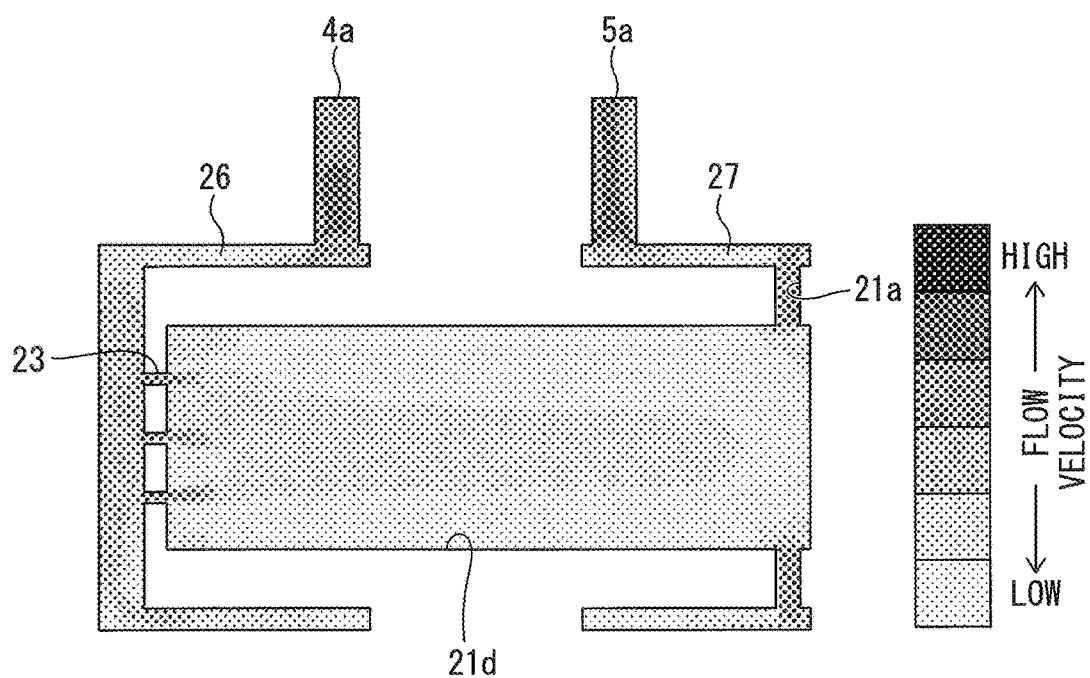
FIG. 13 is a schematic drawing illustrating an example of a fluid simulation result.

FIG. 13 illustrates a fluid simulation result with respect to the fluid sterilization module 1 according to the embodiment of the present invention.

As illustrated in FIG. 13, in a state where the flow velocity is relatively low (for example, over approximately 1 [m/s]), emergence of a turbulent flow was observed in the first chamber 26. In other words, it has been confirmed that the biofilm is unlikely to be generated. Here, FIG. 13 is a simplified drawing of the fluid sterilization module 1.

Example C

A simulation was performed with respect to the fluid sterilization module 1 according to the embodiment of the present invention, to explain the relation between the cross-sectional area A26 of the first chamber 26 and the cross-sectional area A21 of the processing flow path 21d, illustrated in FIG. 2B.

As illustrated in FIGS. 14A to 14C, the three fluid sterilization modules 1-1 to 1-3, each including the inner cylinder 21 of a different outer diameter φD1, were employed, to measure the flow velocity in the communication interface between the inflow portion 4 and the first chamber 26.

In each of the fluid sterilization modules 1-1 to 1-3, the inner diameter φd1 of the inner cylinder 21 was set to φ20 [mm], and the inner diameter φd2 of the case portion 22 was set to φ34 [mm]. The outer diameter φD1 of the inner cylinder 21 of the fluid sterilization module 1-1 was set to φ31 [mm], and the ratio of the cross-sectional area A26 of the first chamber 26 to the cross-sectional area A21 of the processing flow path 21d (A26/A21) was 48.8[%]. The outer diameter φD1 of the inner cylinder 21 of the fluid sterilization module 1-2 was set to φ28 [mm], and the ratio of the cross-sectional area A26 of the first chamber 26 to the cross-sectional area A21 of the processing flow path 21d (A26/A21) was 93[%]. The outer diameter φD1 of the inner cylinder 21 of the fluid sterilization module 1-3 was set to φ26 [mm], and the ratio of the cross-sectional area A26 of the first chamber 26 to the cross-sectional area A21 of the processing flow path 21d (A26/A21) was 120[%].

FIGS. 14A to 14C respectively illustrate the flow velocity distribution in the flow path, with respect to the fluid sterilization modules 1-1 to 1-3. Here, FIGS. 14A to 14C are simplified drawings of the fluid sterilization module 1 illustrated in FIG. 2A.

It has been confirmed, with respect to the fluid sterilization modules 1-1 and 1-2, in which the ratio A26/A21 of the cross-sectional area is smaller than 1, that the minimum the flow velocity in the communication interface K between the inflow portion 4 and the first chamber 26 is higher than 1 [m/sec], and that therefore the generation of the biofilm can be effectively suppressed.

In contrast, with respect to the fluid sterilization module 1-3, in which the ratio A26/A21 of the cross-sectional area is larger than 1, it has been confirmed that the minimum flow velocity in the communication interface between the inflow portion 4 and the first chamber 26 is lower than 1 [m/sec], and that therefore the fluid sterilization module may fail to prevent the generation of the biofilm.

In view of the above, it is understood that, to suppress the generation of the biofilm, it is preferable that the ratio (A26/A21) of the cross-sectional area A26 of the first chamber 26 to the cross-sectional area A21 of the processing flow path 21$d$ is smaller than 1.

REFERENCE SIGNS LIST

1 Fluid sterilization module
2 Sterilization processing unit
3 Light emitting unit
4 Inflow portion
5 Outflow portion
21 Inner cylinder
21$d$ Processing flow path
22 Case portion
23 Plate for flow straightening
24 Member (Annular member)
26 First chamber
27 Second chamber
34 Light source
34$a$ Light emitting element

The invention claimed is:

1. An ultraviolet light irradiation device comprising:
a cylindrical portion forming a cylindrical processing flow path extending in a longitudinal direction;
a case portion in which the cylindrical portion is accommodated;
a member of an annular shape, provided in close contact between an outer circumferential surface of the cylindrical portion and an inner circumferential surface the case portion, and including an elastic member at least in a portion in contact with the inner circumferential surface of the case portion;
a first chamber located in a region on a side of one end portion of the cylindrical portion with respect to the member, in a cylindrical gap between the cylindrical portion and the case portion;
a second chamber located in a region on a side of the other end portion of the cylindrical portion with respect to the member, in the cylindrical gap between the cylindrical portion and the case portion;
an inflow portion through which an object flows into the first chamber;
an outflow portion through which the object flows out of the second chamber; and
a light emitting element provided at least in one of the one end portion and the other end portion of the cylindrical portion, and configured to emit ultraviolet light to the object passing through the processing flow path.

2. The ultraviolet light irradiation device according to claim 1,
wherein the member includes an elastic member provided between the outer circumferential surface of the cylindrical portion and the inner circumferential surface of the case portion.

3. The ultraviolet light irradiation device according to claim 1,
wherein the member is formed integrally with the cylindrical portion on the outer circumferential surface of the cylindrical portion, and an annular elastic member is provided on an outer circumferential surface of the member.

4. The ultraviolet light irradiation device according to claim 1, further comprising a communication port provided in the cylindrical portion to communicate between the processing flow path and the second chamber,
wherein the object in the processing flow path flows out to the second chamber, only through the communication port.

5. The ultraviolet light irradiation device according to claim 1,
wherein the outer circumferential surface of the cylindrical portion is lower in static friction coefficient, than the inner circumferential surface of the case portion.

6. The ultraviolet light irradiation device according to claim 5,
wherein the static friction coefficient of the outer circumferential surface of the cylindrical portion equal to or lower than ½ of the static friction coefficient of the inner circumferential surface of the case portion.

7. An ultraviolet light irradiation device comprising:
a cylindrical portion forming a cylindrical processing flow path extending in a longitudinal direction, and having an opening in one end portion;
a first chamber communicating with the processing flow path via the opening;
an inflow portion through which an object flows into the first chamber;
a second chamber provided along an outer circumferential surface of the other end portion of the cylindrical portion;
a communication port provided in the cylindrical portion, to communicate between the processing flow path and the second chamber;
an outflow portion through which the object that has passed through the processing flow path flows out from the other end portion of the cylindrical portion; and
a light emitting element provided at least in one of the one end portion and the other end portion of the cylindrical portion, and configured to emit ultraviolet light to the object passing through the processing flow path,
wherein the object in the processing flow path flows into the second chamber, only through the communication port.

8. The ultraviolet light irradiation device according to claim 7,
wherein the cylindrical portion includes a member located at an end face of the other end portion, and configured to cover an entirety of an opening in the other end portion, and
the member and the end portion of the cylindrical portion are joined to each other via an elastic member.

9. The ultraviolet light irradiation device according to claim 8,
wherein the elastic member includes an elastomer.

10. The ultraviolet light irradiation device according to claim 8,
wherein the elastic member includes one of a silicone resin elastomer and a fluororesin elastomer.

11. The ultraviolet light irradiation device according to claim 1,
wherein a variation range of a main cross-sectional area of the processing flow path from a most upstream portion to a most downstream portion is equal to or lower than 5%.

12. The ultraviolet light irradiation device according to claim 1,
wherein, in a cross-section orthogonal to the longitudinal direction at a position in the cylindrical portion including the first chamber, a cross-sectional area of the first chamber is equal to or larger than 1/10, and equal to or smaller than 1, of a cross-sectional area of the processing flow path.

13. The ultraviolet light irradiation device according to claim 1,
wherein the cylindrical portion includes an ultraviolet light reflecting material having a diffuse transmittance equal to or higher than 1[%]/1 [mm], and equal to or lower than 20[%]/1 [mm], and a total reflectance in an ultraviolet light region equal to or higher than 80[%]/1 [mm], and equal to or lower than 99[%]/1 [mm].

14. The ultraviolet light irradiation device according to claim 13,
wherein a sum of the diffuse transmittance and total reflectance in the ultraviolet light region is equal to or larger than 90[%]/1 [mm].

15. The ultraviolet light irradiation device according to claim 13,
wherein the ultraviolet light reflecting material includes at least one of polytetrafluoroethylene, a silicone resin, quartz glass containing an air bubble equal to or larger than 0.05 [μm] and equal to or smaller than 10 [μm], partially crystallized quartz glass containing crystallized particles equal to or larger than 0.05 [μm] and equal to or smaller than 10 [μm], an alumina sintered compact including crystallized particles equal to or larger than 0.05 [μm] and equal to or smaller than 10 [μm], and a mullite sintered compact including crystallized particles equal to or larger than 0.05 [μm] and equal to or smaller than 10 [μm].

16. The ultraviolet light irradiation device according to claim 1,
wherein a wall thickness of the cylindrical portion is equal to or thicker than 1 [mm], and equal to or thinner than 20 [mm].

17. The ultraviolet light irradiation device according to claim 1, configured as a fluid sterilization module.

18. The ultraviolet light irradiation device according to claim 1,
wherein the inflow portion includes polyolefin.

19. The ultraviolet light irradiation device according to claim 1,
wherein the object includes a liquid.

* * * * *